United States Patent [19]
Tabuse et al.

[11] Patent Number: 5,877,496
[45] Date of Patent: Mar. 2, 1999

[54] APPARATUS AND METHOD FOR ANALYSIS OF SURFACE IMPURITIES IN A VERY SMALL REGION

[75] Inventors: Kazuhiko Tabuse; Masao Watanabe, both of Tokyo, Japan

[73] Assignee: Advantest Corporation, Tokyo, Japan

[21] Appl. No.: 860,926

[22] PCT Filed: Nov. 21, 1996

[86] PCT No.: PCT/JP96/03406

§ 371 Date: Jul. 21, 1997

§ 102(e) Date: Jul. 21, 1997

[87] PCT Pub. No.: WO97/19343

PCT Pub. Date: May 29, 1997

[30] Foreign Application Priority Data

Nov. 21, 1995 [JP] Japan .................................. 7-302889

[51] Int. Cl.$^6$ .................................................. H01J 49/00
[52] U.S. Cl. .................................................. 250/288
[58] Field of Search .............................. 250/288, 288 A, 250/281, 282, 310

[56] References Cited

U.S. PATENT DOCUMENTS

| | | | |
|---|---|---|---|
| 4,393,311 | 7/1983 | Feldman et al. | 250/310 |
| 4,968,888 | 11/1990 | Appelhans et al. | 250/288 |
| 5,650,616 | 7/1997 | Iketaki | 250/288 |

*Primary Examiner*—Kiet T. Nguyen
*Attorney, Agent, or Firm*—Oblon, Spivak, McClelland, Maier & Neustadt, P.C.

[57] ABSTRACT

An analysis method by which a surface impurity in a very small region can be specified, wherein an electron beam is accelerated with an acceleration voltage and irradiated upon a very small region of a specimen and a mass spectrometry of neutral surface impurity molecules desorbed from the very small region is performed. The acceleration voltage for accelerating the electron beam is set to a voltage with which desorption of the neutral surface impurity molecules by an electron stimulated desorption (ESD) effect occurs.

12 Claims, 7 Drawing Sheets

APPARATUS AND METHOD FOR ANALYSIS OF SURFACE IMPURITIES IN A VERY SMALL REGION

TECHNICAL FIELD

This invention relates to a measurement method and apparatus for analyzing surface impurities in a very small region, and more particularly to an apparatus and an analysis method for a surface impurities for use to analyze a surface impurity on an electronic circuit part, a relay contacting surface, an integrated circuit device or any other very small electronic part to analyze a cause of a failure arising from deterioration by contamination.

BACKGROUND ART

A failure in operation of an electronic circuit part, a relay contacting surface, an integrated circuit device such as an IC or an LSI or any other very small electronic part is caused in most cases by a contaminating impurity sticking to the surface.

Contaminating impurities can be roughly divided into the following three:

(1) organic molecules including negative atoms such as oxygen, chlorine or sulfur;

(2) hydrocarbon molecules; and (3) organic molecules which include both of nitrogen and oxygen.

Since the cause of a failure in operation which takes place is different depending upon the type of the contaminating impurity, it is important and necessary to specify what the contaminating impurity is.

As methods of analyzing a contaminating impurity sticking to the surface of an object, a reflection type infrared absorption method, an ion irradiation mass spectrometry method and a slow electron energy loss analysis method are practically used. However, while those analysis methods are all applied where the analysis surface area for which it is required to perform an analysis is approximately $(0.1 \text{ mm})^2$ to (several mm)$^2$, in order to analyze the surface of a chip of a semiconductor device at present, the analysis surface area is required to be on the order lower than $(\mu m)^2$. Accordingly, any of the analysis methods described above is not suitably used to analyze the surface of an electronic part.

Also a different method is available wherein an electron beam is irradiated upon the surface of a specimen and desorbed molecules are analyzed using a mass spectrograph. In this instance, it is possible to concentrate energy upon a very small region on the order lower than $(\mu m)^2$ from a relationship of an electron wavelength, and it is possible to analyze the very small region.

From among the conventional analysis methods described above, the reflection type infrared absorption method, the ion irradiation mass spectrometry method and the slow electron energy loss analysis method are not suitable to analyze the surface of an electronic part since the area required for the analysis is large.

The method wherein an electron beam is irradiated and desorbed molecules are analyzed using a mass spectrograph allows an analysis of a very small region. However, the method has a problem in that, where different molecules have an equal mass number (for example, $CH_4$ and O, $CH_4OH$ and $O_2$, and so forth), it cannot be specified what the contaminating impurity is.

DISCLOSURE OF THE INVENTION

The present invention has been made in view of such problems of the prior art as described above, and it is an object of the present invention to provide an analysis method by which a surface impurity in a very small region can be specified.

According to the present invention, an analysis method for a surface impurity in a very small region wherein an electron beam is accelerated with an acceleration voltage and irradiated upon a very small region of a specimen and a mass spectrometry of surface impurity molecules desorbed from the very small region is performed, is characterized in that the acceleration voltage for accelerating the electron beam is set to a voltage with which desorption of surface contaminating molecules by an ESD effect occurs.

According to the present invention, another analysis method for a surface impurity in a very small region which is performed by an analysis apparatus which has both of an Auger electron spectral diffraction measurement function and a mass spectrometry measurement function and wherein an electron beam is accelerated and irradiated upon a very small region of a specimen to desorb surface impurity molecules in the very small region to analyze the surface impurity molecules, is characterized in that an acceleration voltage for accelerating the electron beam is set to a voltage with which desorption of surface contaminating molecules by an ESD effect occurs, and an Auger electron spectral diffraction measurement is performed simultaneously.

In this instance, the electron beam may be irradiated upon the very small region of the specimen by a plurality of times successively changing the acceleration voltage for accelerating the electron beam.

Or, the acceleration voltage for accelerating the electron beam may be set to a voltage with which an intermediate electron beam by which desorption of surface contaminating molecules by an indirect ESD effect is caused is generated.

Further, irradiation of an electron beam with an acceleration voltage of 0.5 KeV to 1.2 KeV, irradiation of another electron beam with another acceleration voltage of 1.4 KeV to 2.4 KeV and irradiation of a further electron beam with a further acceleration voltage of 2.8 KeV or more may be performed.

According to the present invention, an analysis apparatus for a surface impurity in a very small region wherein an electron beam is accelerated with an acceleration voltage and irradiated upon a very small region of a specimen and a mass spectrometry of surface impurity molecules desorbed from the very small region is performed, is characterized in that it comprises acceleration voltage control means for adjusting the acceleration voltage for accelerating the electron beam.

The present invention has been made taking notice of a molecular desorption phenomenon by an ESD (Electron Stimulated Desorption) effect by irradiation of an electron beam.

A desorption mechanism by an ESD effect is described below.

Molecules whose bonding orbitals have been cut by irradiation of an electron beam are driven into an excited state and oscillated, so that those molecules which are desorbed from the surface having a neutral or ionization potential are generated. The ratio of the neutral desorbed molecules to the ionization desorbed molecules then is such that the neutral desorbed molecules are 100 times or more the ionization desorbed molecules, so it can be said that almost all desorbed molecules are neutral desorbed molecules.

Such a desorption mechanism by excitation as described above is called direct ESD effect and is generated by a slow electron beam whose acceleration voltage is approximately 100 to 500 eV.

In contrast with the direct ESD effect, also an indirect ESD effect which is caused by an intermediate electron beam whose acceleration voltage is approximately 0.5 to 3 KeV is known. Where an intermediate electron beam is used, since the scattering cross section by surface molecules is small, the probability that molecules may be excited directly is low, but the energy of inelastic scattering electrons is distributed widely and also a large number of electrons whose energy is lower than 500 eV are generated. Molecules are excited by such electrons generated secondarily by collision of an intermediate electron beam and having energy lower than 500 eV, producing desorbed molecules.

The inventors have perceived that, different from ordinary thermal desorption, in desorption of molecules by an ESD effect, organic molecules to be desorbed are different in type depending upon the acceleration energy for an electron beam.

Conventionally, in an apparatus which employs a scanning electron microscope (hereinafter referred to as SEM) or an Auger electron spectroscopy (hereinafter referred to as AES), adjustment of an acceleration voltage is performed in order to vary the magnification or the resolution, and a measurement itself is performed with an equal acceleration voltage. In contrast, in the present invention, based on the perception obtained by the investigation, acceleration voltages with which desorption of organic molecules containing oxygen, hydrocarbon molecules and organic molecules containing nitrogen or oxygen occurs significantly are successively irradiated to individually perform a mass spectroscopy. Consequently, identification of organic molecules which have an equal mass number but are different in type is allowed.

Further, where an intermediate electron beam is irradiated, desorbed molecules by an indirect ESD effect are generated and observation by means of an SEM or a measurement based on an AES is allowed, and a mass spectroscopy can be performed together with those operations.

BRIEF DESCRIPTION OF DRAWINGS

FIG. 2($a$) is a view showing a partial construction of the embodiment shown in FIG. 1 in more detail, and FIG. 2($b$) is a view showing a construction of a conventional example as a comparative example with the construction shown in FIG. 2($a$);

FIGS. 5($a$) to 5($d$) are diagrams illustrating ion currents when ions are irradiated varying the acceleration voltage;

FIGS. 7($a$) to 7($c$) are diagrams illustrating desorption states by the present invention when molecules are desorbed by an ESD effect, particularly by an indirect ESD effect, and FIG. 7($d$) is a diagram illustrating a desorption state of molecules by thermal desorption as a comparative example.

BEST MODE FOR CARRYING OUT THE INVENTION

In the following, an embodiment of the present invention is described with reference to the drawings.

Figure 1:
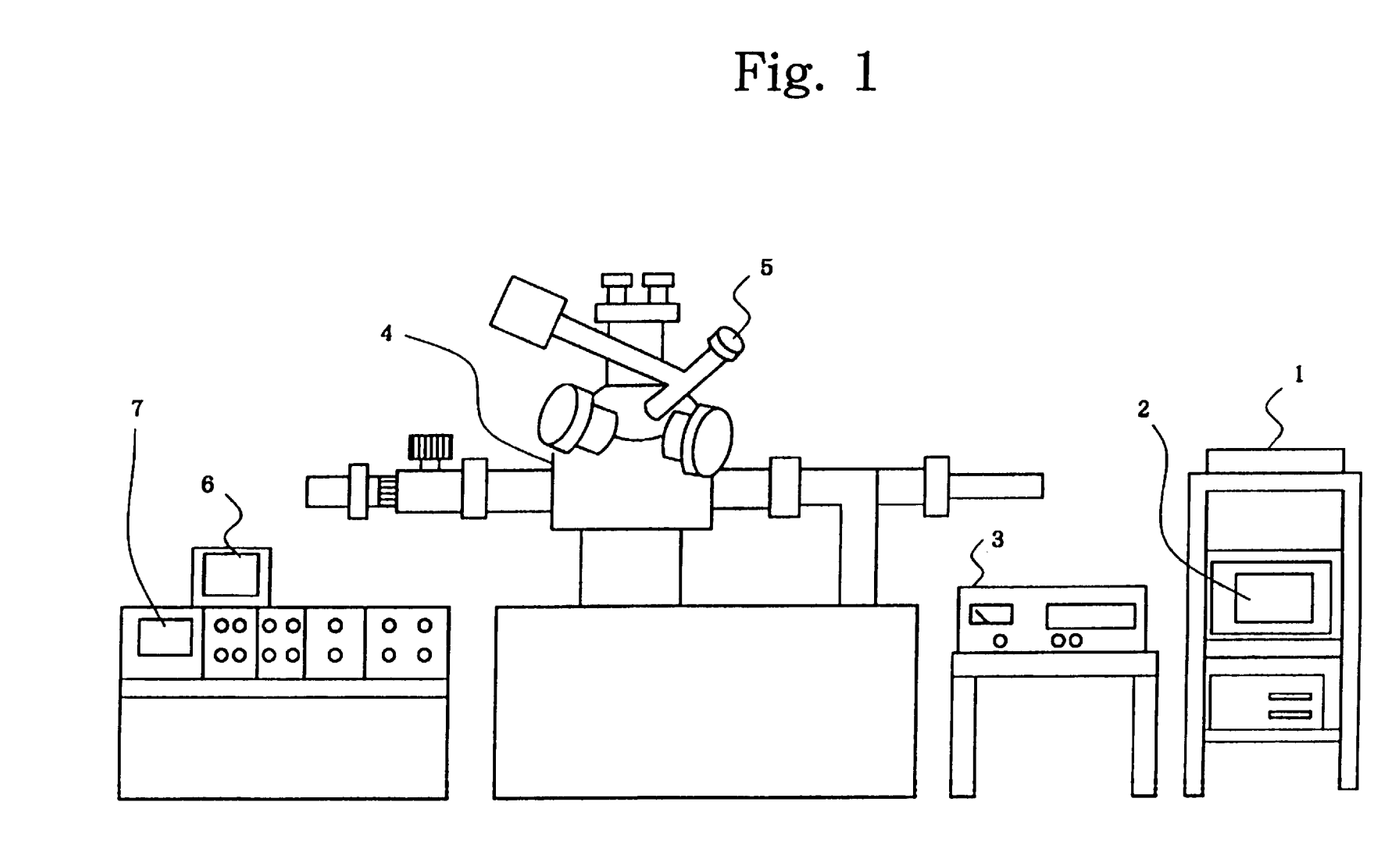
FIG. 1 is a view of an appearance showing a construction of an apparatus on which a measurement method according to the present invention is carried out.

FIG. 1 is a view showing a construction of an apparatus on which a measurement method according to the present invention is carried out.

The present embodiment includes mass spectrometric detector 5 mounted on a composite apparatus which employs an SEM and another apparatus which is based on an AES and allows an analysis by an AES and a mass spectrometry of a specimen placed in chamber 4. Spectrum images indicating results of the analyses are displayed on monitor 7 and monitor 2, respectively. Meanwhile, a surface observation image by an SEM is displayed on monitor 2. For a generation source for an electron beam to be used for a mass spectrometry, the same generation source as that for Auger electron spectral diffraction is used, and molecules generated by irradiation of the electron beam and detected by mass spectrometric detector 5 are analyzed by mass spectrometry unit 3 and a result of the analysis is displayed on monitor 2.

Figure 2:
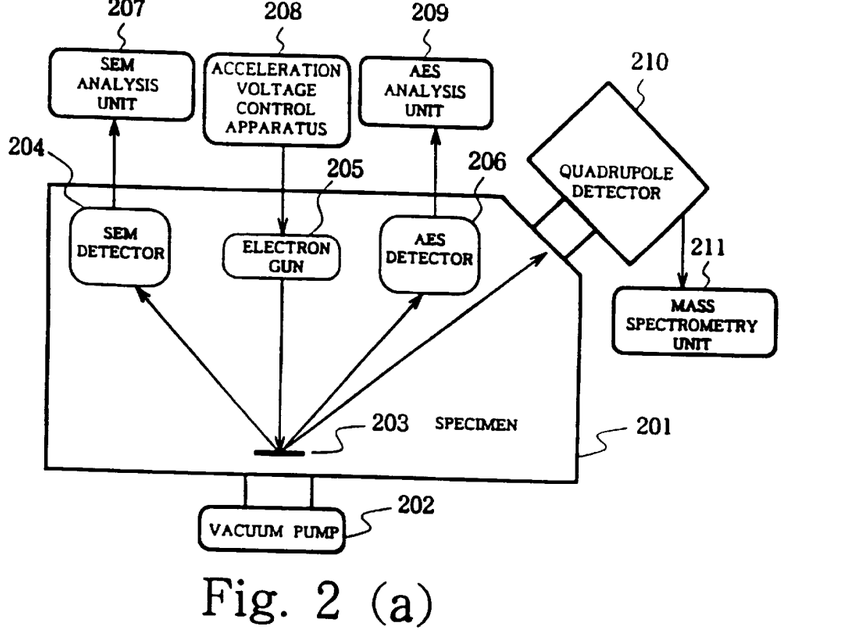

FIG. 2($a$) is a view showing a construction of the apparatus which employ an SEM and an AES and the mass spectrograph in the present embodiment in more detail including elements which are omitted in FIG. 1, and FIG. 2($b$) is a view showing a construction of a conventional example as a comparative example.

In chamber 201 (chamber 4 in FIG. 1) which has been evacuated by vacuum pump 202 and in which specimen 203 which is an object of measurement is disposed, electron gun 205 for irradiating an electron beam upon specimen 203, SEM detector 204, AES detector 206 and quadrupole detector 210 for a mass spectrometry (mass spectrometric detector 5 in FIG. 1) are provided. Contents of detection of SEM detector 204, AES detector 206 and quadrupole detector 210 are sent to and analyzed by SEM analysis unit 207, AES analysis unit 209 and mass spectrometry unit 211 (mass spectrometry unit 3 in FIG. 1), and a result of the analysis by AES analysis unit 209 is displayed on monitor 7 of FIG. 1 while results of the analyses by SEM analysis unit 207 and mass spectrometry unit 211 are displayed on monitor 2 of FIG. 1.

As described above, the present invention is characterized in that molecules are selectively desorbed by an indirect ESD effect when the acceleration voltage for an electron beam is varied, and in order to realize this, in FIG. 2($a$), acceleration voltage control apparatus 208 for adjusting the acceleration voltage of electron gun 205, which is not provided in the conventional example shown in FIG. 2($b$), is provided.

As operation modes of the apparatus shown in FIG. 1, a mass spectrometry mode, an Auger electron spectral diffraction mode, an observation mode in which an SEM is used and so forth are available, and operation control in each mode is performed by control apparatus 1. Control apparatus 1 changes the operation mode in response to contents of an input by a user of the apparatus and determines the acceleration voltage for an electron beam to be emitted from electron gun 205 via acceleration voltage control apparatus 208.

In order to perform an analysis of a very small region whose analysis surface area is on the order lower than $(\mu m)^2$, energy must be irradiated locally to desorb molecules. Here, it is possible to concentrate energy on a very small region on the order lower than $(\mu m)^2$ by adopting a technique of irradiating an electron beam. Further, in order to assure an accurate measurement and analysis without being influenced by the background, chamber 4 in which a specimen is to be placed is in an ultra-high vacuum state on the order of $10^{-10}$ Torr.

A gas introduction pipe which communicates chamber 4 and mass spectrometric detector 5 with each other is made of an aluminum alloy in order to prevent such a situation that a desorbed impurity is caught by a wall surface of the gas introduction pipe or replaced by some other molecules. Further, by observing an SEM image, a very small measurement location can be specified.

Of the operation modes of the analysis apparatus for a surface impurity in a very small region shown in FIG. 1, the observation operation by an SEM is described first.

The SEM apparatus is used to specify the surface of a specimen to be analyzed. This SEM apparatus accelerates thermions generated by an electron beam generating filament serving as a generation source of an electron beam with a high voltage of approximately 3 kV and converges the thermions by means of a condenser lens so that the thermions may collide as a primary electron beam with the specimen. The SEM apparatus detects a secondary electron beam emitted from the specimen as a result of the collision of the primary electron beam, specifies it as a location at which the primary electron beam has collided, and converts it into image information. An image based on the image information is displayed on monitor 6.

The emission probability of secondary electrons depends upon the work function of the specimen, the surface impurity amount and the surface configuration of the specimen. Accordingly, by scanning the surface of the specimen with the primary electron beam, a contrast according to the surface state can be obtained to effect image observation. The surface of the specimen to be analyzed can be specified by the observation.

Next, a mass spectrometry operation is described.

The mass spectrograph includes an ion source for ionizing and extracting gas molecules in a fixed direction, and an analysis unit for analyzing the ion beam in accordance with the value of the electron charge ratio m/e, and may be of the quadrupole type, the magnetic field deflection type or some other type depending upon the type of the analysis unit. A mass spectrograph of the magnetic field deflection type analyzes making use of the fact that the locus of a charged particle passing therethrough is varied depending upon the value of m/e. In the present embodiment, a mass spectrograph of the quadrupole type which analyzes an ion locus using an electric field formed by four electrodes.

As an electron beam collides with a specimen, desorbed molecules are generated and emitted from the surface of the specimen. The desorbed molecules are fed by the gas introduction pipe, which is made of an aluminum alloy and communicates chamber 4 and mass spectrometric detector 5 with each other, into and detected by mass spectrometric detector 5 and then analyzed by mass spectrometry unit 3. As a result of the analysis, the mass number, signal intensity and so forth are displayed on monitor 2.

Where the bond between a substrate made of a metal or a semiconductor and organic impurity molecules sticking to the surface is weak, desorbed impurities diffuse spherically and isotropically from an accelerated electron colliding point. Where the bond is strong, desorbed impurity molecules are desorbed in a direction which depends upon the direction of molecule oscillations. When fast electrons collide with the surface of the substrate, the surface temperature rises, but in this instance, sticking molecules are desorbed as they are while remaining in the form of molecules. When the energy of incident electrons is high, sticking molecules are in most cases desorbed as they are while remaining in the form of molecules.

When an electron beam is irradiated upon a specimen, an impurity sticking to the surface is desorbed and emitted from the surface of the specimen. Molecules of the organic impurity desorbed from the surface of the specimen collide with fast electrons and are partly decomposed, so that they are detected in the form of H, $H_2$, OH, CO or other atoms or molecules as described above. However, the molecules of the desorbed organic impurity collide, when they are introduced into the gas introduction pipe, with the inner wall surface of the pipe and are partly attracted by the inner wall surface. Thereupon, replacement of $H_2O$, $O_2$, $CO_2$ or other substances which have already been absorbed into the inner wall surface of the pipe with molecules of the desorbed organic impurity takes place. However, since the gas introduction pipe is made of an aluminum alloy and the inner wall surface of the pipe has already changed to alumina, both the number of kinds and the amount of substances absorbed into the surface are small comparing with those of a gas introduction pipe made of a material of stainless steel or the like, and the possibility that the replacement of molecules to be measured may have a bad influence on a result of measurement is decreased.

Figure 3:
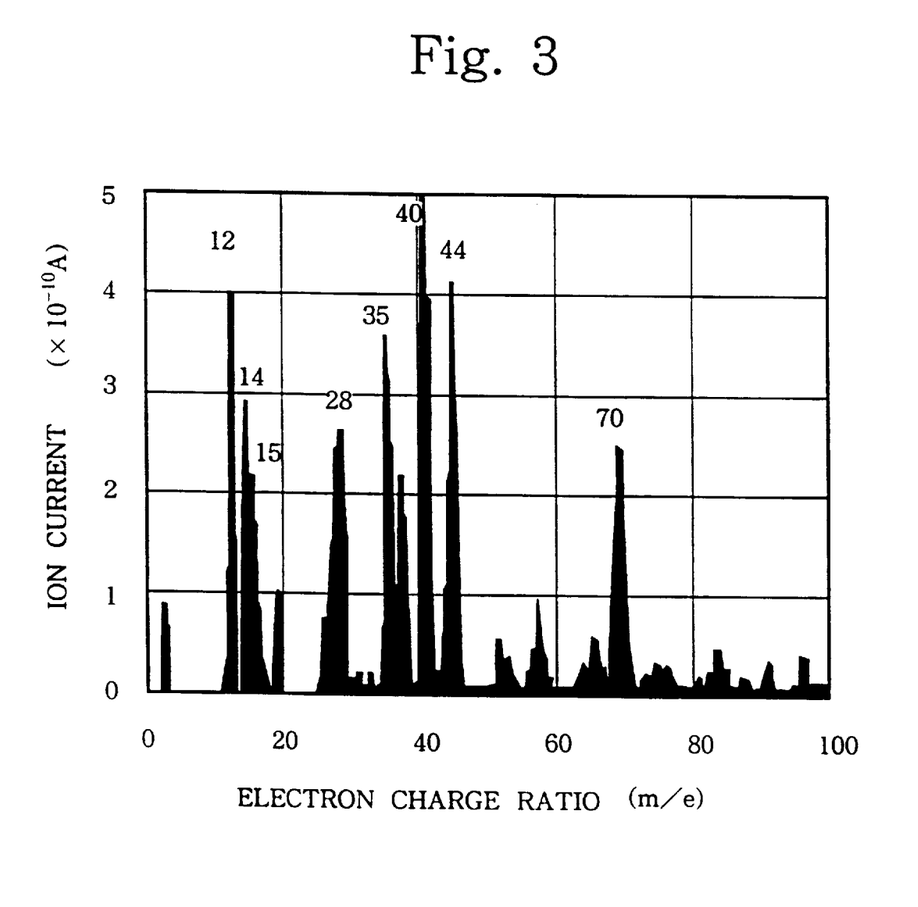
FIG. 3 is a diagram showing a mass spectrum obtained when molecules from the surface of an Al wire are desorbed.

FIG. 3 shows a mass spectrum obtained when molecules are desorbed from the surface of an Al wire. It can be seen that the mass spectrum has a peak in the proximity of the mass number 2 and hydrogen atoms or molecules are present. And, a plurality of peaks are present within the range of the mass numbers 16 through 18 and it is supposed that methane gas, a hydroxyl group or water molecules are present. Further, it is supposed that the peak in the proximity of the mass number 28 is provided by carbon monoxide, the peak in the proximity of the mass number 35 is provided by chlorine, and the peak in the proximity of the mass number 45 is provided by carbon dioxide. After all, it is determined that, as original molecules, $H_2$, $H_2O$, $CO_2$, $Cl_2$ and $CH_4$ were present.

Figure 4:
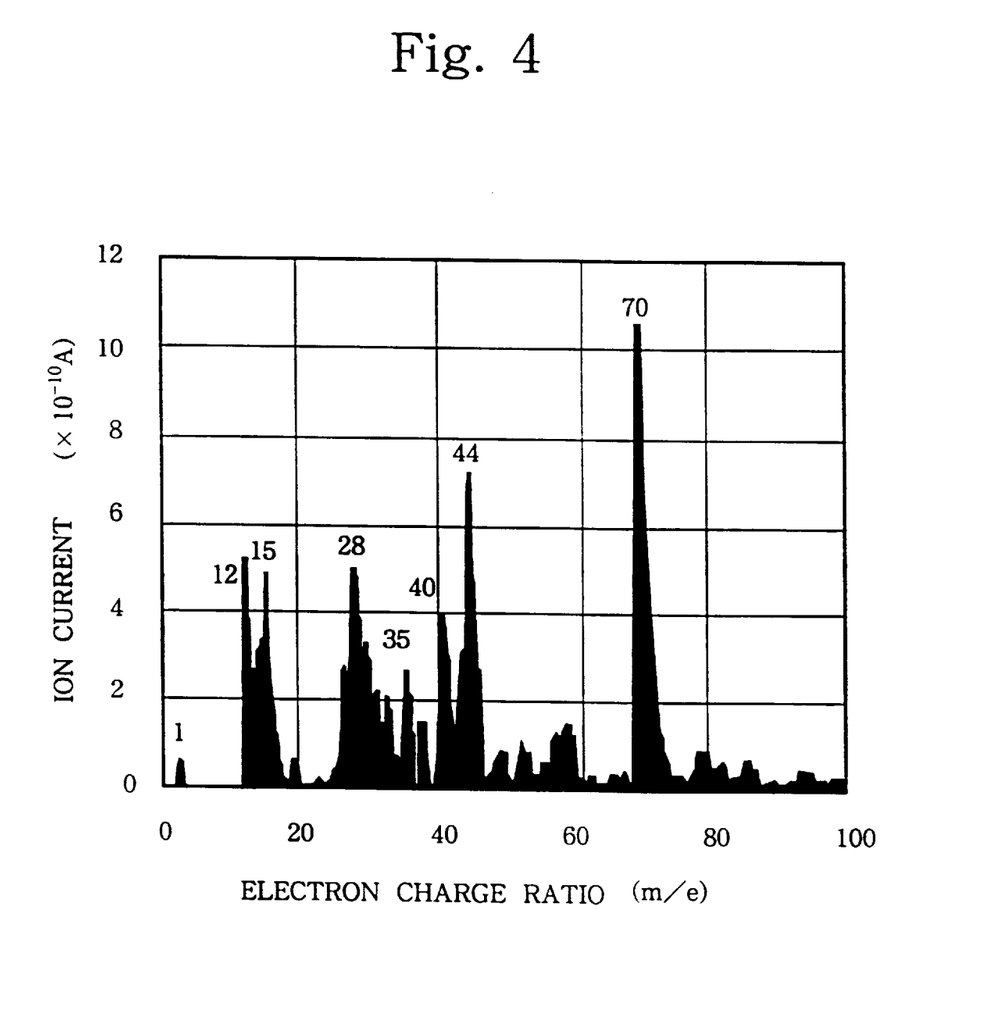
FIG. 4 is a diagram showing a mass spectrum obtained when the Al wire shown in FIG. 3 absorbs polystyrene dissolved in acetone solvent to desorb molecules.

FIG. 4 shows a mass spectrum obtained when polystyrene is absorbed into the Al wire shown in FIG. 3 to desorb molecules desorbed from the Al wire. It can be seen that, as a result of the absorption of polystyrene, atoms or molecules which compose the styrene have been decomposed.

According to the present invention, taking notice of the fact that a desorption phenomenon of organic molecules containing oxygen, hydrocarbon molecules or organic molecules containing nitrogen or oxygen which make an object of analysis is varied by an ESD effect when the acceleration voltage for an electron beam is varied, particularly by an indirect ESD effect, an electron beam is irradiated upon a measurement region while varying the acceleration voltage for an electron beam.

Figure 5:
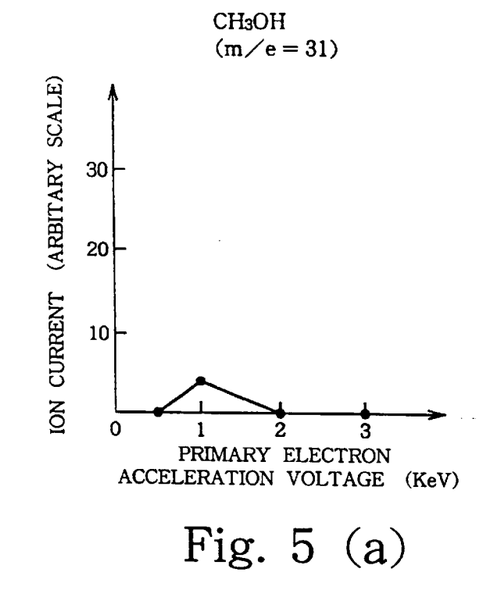

FIG. 5(a) illustrates an ion current when an ion beam is irradiated upon $CH_3OH$ of the mass number 31 as oxygen organic molecules varying the acceleration voltage; FIGS. 5(b) and 5(c) illustrate ion currents when an ion beam is irradiated upon $CH_4$ of the mass number 15 and $CH_3CH=CH_2$ of the mass number 42 as hydrocarbon molecules varying the acceleration voltage; and FIG. 5(d) illustrates an ion current when an ion beam is irradiated upon $CH_2NCO$ of the mass number 56 as organic molecules containing nitrogen or oxygen varying the acceleration voltage. Those substances are selected so that they may not overlap with any other substance present in the chamber.

As seen from FIG. 5(a), it can be seen that, with $CH_3OH$ which is organic molecules containing a hydroxyl group (oxygen), the ion current by electron impact desorption exhibits a maximum value in the proximity of the acceleration voltage of 1 KeV, and little desorption occurs in the proximity of the acceleration voltage of 2 to 3 KeV.

As seen from FIGS. 5(b) and 5(c), with the organic compounds of $CH_4$ and $CH_3CH=CH_2$ which are hydrocarbon molecules only having C—H bonds, the ion current value exhibits a maximum value at the acceleration voltage of 2 KeV, but no desorption occurs at 1 KeV.

As seen from FIG. 5(d), with $CH_2NCO$ which is organic molecules containing nitrogen and oxygen, as the acceleration voltage increases, the desorption phenomenon occurs more remarkably. This arises from the fact that, since, with organic molecules containing nitrogen and oxygen, generally a plurality of chemical bonds are formed on the surface and the bonding force of surface molecules is high, it occurs less likely that surface molecules are driven into an excited state and desorbed by an electron impact. Consequently, different from the examples shown in FIGS. 5(a) to 5(c), the ion current does not exhibit a maximum value at any acceleration voltage, but exhibits a monotone increase as the acceleration voltage increases, and desorption occurs by a heating effect of a metal substrate by an electron beam.

Figure 6:
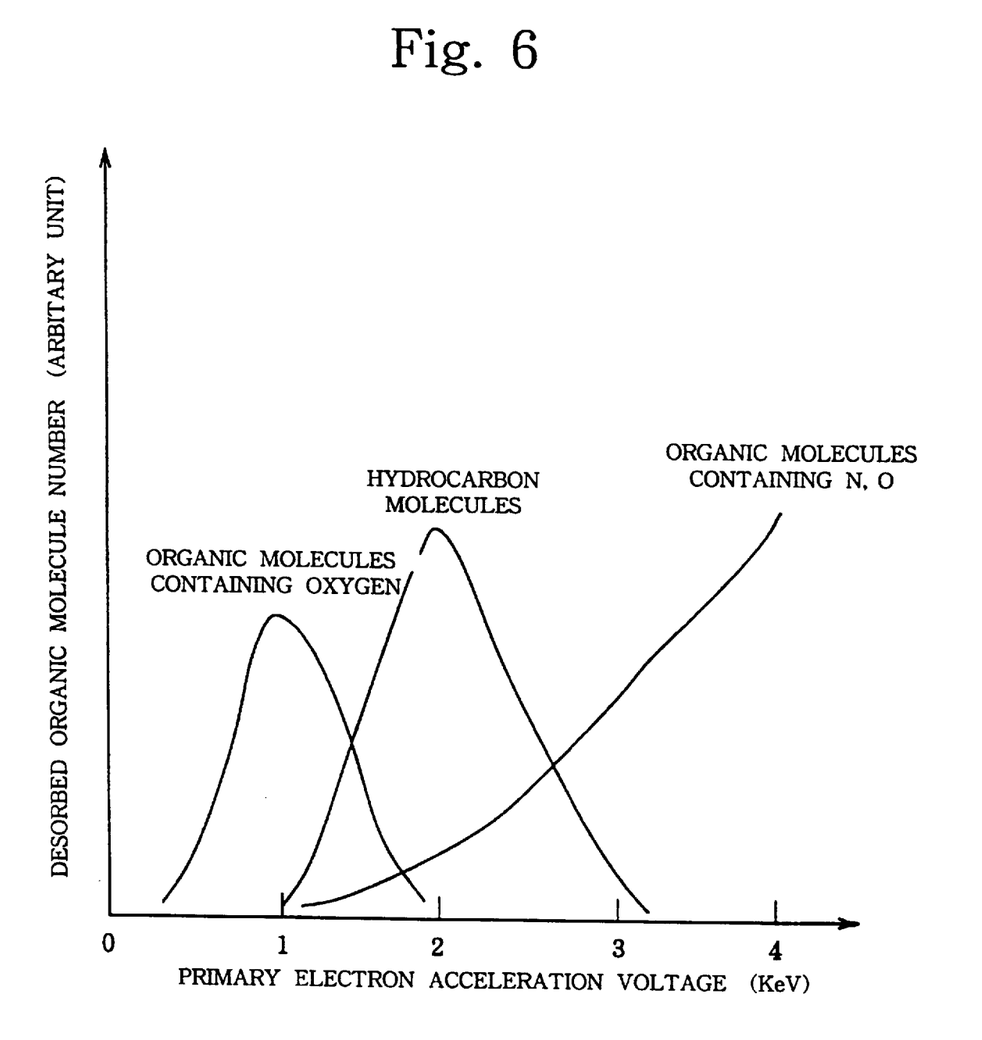
FIG. 6 is a diagram illustrating the desorbed molecule number which varies in accordance with a variation of the acceleration voltage collectively for different kinds of organic compounds.

FIG. 6 is a diagram illustrating the desorbed molecule number which varies in accordance with a variation of the acceleration voltage collectively for different kinds of organic compounds.

Taking such a tendency as described above into consideration, an analysis in the present embodiment is performed in accordance with the following procedure.

(1) First, the apparatus is put into an observation mode by an SEM and specifies a location at which a failure has occurred and for which an analysis is to be performed. In the present embodiment, an electron beam is used to allow an analysis of a very small region, and it is difficult to determine an analysis location at which a failure has occurred. Particularly, in a complicated electronic part of a multi-layer structure such as an LSI, a failure may possibly occur at any of various locations, and it is very difficult to specify a failure location. When to specify a failure location of an LSI or the like, the failure location is roughly specified using an IC tester, and then the failure location is specified rather particularly using an EB tester, whereafter observation in which an SEM is used is performed to finally specify the analysis location.

(2) Then, a mass spectrum is observed successively changing the acceleration voltage for an electron beam to 1 KeV, 2 KeV and 3 KeV. The types of organic molecules desorbed in accordance with the acceleration voltages can be classified as described above, and this allows identification of organic molecules which have an equal mass number but are different in type.

(3) Finally, the apparatus is put into an Auger electron spectral diffraction mode to effect an Auger electron spectral diffraction measurement. Although a measurement of the molecule level cannot be performed by the Auger electron spectral diffraction measurement, a finer analysis is allowed by specifying atoms which compose remaining molecules. It is to be noted that the Auger electron spectral diffusion measurement may be performed simultaneously with the mass spectrometry.

While, in the embodiment described above, the acceleration voltage for an electron beam is changed among 1 KeV, 2 KeV and 3 KeV, since, as seen from FIG. 6, with organic molecules containing oxygen, the desorbed organic molecule number is significantly different at irradiation electron energy of 0.5 KeV to 1.2 KeV from the desorbed organic molecule numbers of the other molecules, with hydrocarbon molecules, the desorbed organic molecule number is significantly different at irradiation electron energy of 1.4 KeV to 2.4 KeV from the desorbed organic molecule numbers of the other molecules, and with organic molecules containing nitrogen and oxygen, the desorbed organic molecule number is significantly different at irradiation electron energy of 2.8 KeV or more from the desorbed organic molecule numbers of the other molecules, the effects by the present invention can be obtained where the acceleration voltage remains within those ranges, and the acceleration voltage is not limited specifically.

Figure 7:
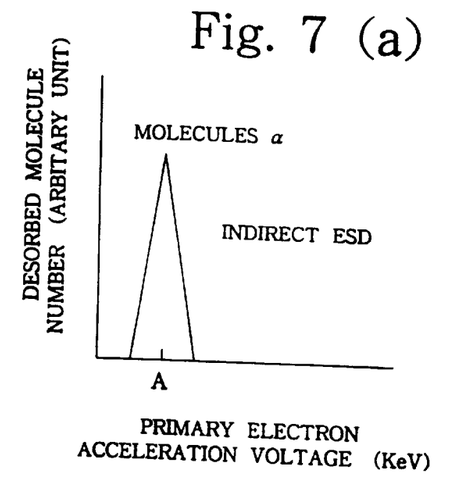

FIGS. 7(a) to 7(c) are diagrams illustrating desorption states by the present invention when molecules are desorbed by an ESD effect, particularly by an indirect ESD effect, and FIG. 7(d) is a diagram illustrating a desorption state of molecules by thermal desorption as a comparative example.

When molecules are desorbed by thermal desorption, the number of desorbed molecules increases in proportion to an increase of the acceleration voltage as seen from FIG. 7(d). However, in the present invention which utilizes an ESD effect, where the acceleration voltage is represented by A, B and C, molecules α,β and γ are selectively separated as seen from FIGS. 7(a), 7(b) and 7(c).

Since the present invention is constructed in such a manner as described above, there is an effect that organic molecules in a very small region which have an equal mass number but are different in type can be identified and an analysis of a cause of occurrence of a failure can be performed with a high degree of accuracy.

We claim:

1. An analysis method for a surface impurity, comprising the steps of:

accelerating an electron beam with an acceleration voltage;

irradiating the accelerated electron beam upon a very small region of a specimen;

performing a mass spectrometry of neutral surface impurity molecules desorbed from the very small region;

wherein the accelerating step includes the step of setting the acceleration voltage to a voltage with which desorption of the neutral surface impurity molecules by an electron stimulated desorption (ESD) effect occurs.

2. The analysis method according to claim 1, wherein the irradiating step includes the step of irradiating the electron beam upon the very small region of the specimen a plurality of times by successively changing the acceleration voltage for accelerating the electron beam.

3. The analysis method according to claim 2, wherein the irradiating step, includes the steps of, irradiating an electron beam with an acceleration voltage of 0.5 KeV to 1.2 KeV, irradiating another electron beam with another acceleration voltage of 1.4 KeV to 2.4 KeV, and irradiating a further electron beam with a further acceleration voltage of 2.8 KeV or more.

4. The analysis method according to claim 1, wherein the accelerating step includes the step of setting the acceleration voltage to a voltage with which an intermediate electron beam by which desorption of the neutral surface impurity molecules by an indirect ESD effect is generated.

5. An analysis method for a surface impurity, comprising the steps of:

accelerating an electron beam with an acceleration voltage;

irradiating the accelerated electron beam upon a very small region of a specimen to desorb neutral surface impurity molecules in the very small region; and analyzing the neutral surface impurity molecules desorbed from the very small region by performing a mass spectrometry measurement;

wherein the accelerating step includes the step of setting the acceleration voltage to a voltage with which desorption of the neutral surface impurity molecules by an electron stimulated desorption (ESD) effect occurs, and performing an Auger electron spectral diffraction measurement simultaneously therewith.

6. The analysis method according to claim 5, wherein the irradiating step includes the step of irradiating the electron beam upon the very small region of the specimen a plurality of times by successively changing the acceleration voltage for accelerating the electron beam.

7. The analysis method according to claim 5, wherein the accelerating step includes the step of setting the acceleration voltage to a voltage with which an intermediate electron beam by which desorption of the neutral surface impurity molecules by an indirect ESD effect is generated.

8. The analysis method according to claim 5, wherein the irradiating step, includes the steps of, irradiating an electron beam with an acceleration voltage of 0.5 KeV to 1.2 KeV, irradiating another electron beam with another acceleration voltage of 1.4 KeV to 2.4 KeV, and irradiating a further electron beam with a further acceleration voltage of 2.8 KeV or more.

9. An analysis apparatus for a surface impurity, comprising:

means for accelerating an electron beam with an acceleration voltage;

means for irradiating the accelerated electron beam upon a very small region of a specimen;

means for performing a mass spectrometry of neutral surface impurity molecules desorbed from the very small region; and an acceleration voltage control means for adjusting the acceleration voltage for accelerating the electron beam to a voltage with which desorption of the neutral surface impurity molecules by an electron stimulated desorption (ESD) effect occurs.

10. The analysis apparatus according to claim 9, wherein the irradiating means includes means for irradiating the electron beam upon the very small region of the specimen a plurality of times by successively changing the acceleration voltage for accelerating the electron beam.

11. The analysis apparatus according to claim 10, wherein the irradiating means, includes, means for irradiating an electron beam with an acceleration voltage of 0.5 KeV to 1.2 KeV, means for irradiating another electron beam with another acceleration voltage of 1.4 KeV to 2.4 KeV, and means for irradiating a further electron beam with a further acceleration voltage of 2.8 KeV or more.

12. The analysis apparatus according to claim 9, wherein the accelerating means includes means for setting the acceleration voltage to a voltage with which an intermediate electron beam by which desorption of the neutral surface impurity molecules by an indirect effect is generated.

* * * * *